United States Patent
Ingram et al.

(10) Patent No.: US 6,733,794 B1
(45) Date of Patent: May 11, 2004

(54) TOPICAL COMPOSITION FOR ANTISEPTIC AND ANALGESIC PURPOSES

(76) Inventors: Edward L. Ingram, P.O. Box 24102, Savannah, GA (US) 31403; Mary Scott, P.O. Box 24102, Savannah, GA (US) 31403

( * ) Notice: Subject to any disclaimer, the term of this patent is extended or adjusted under 35 U.S.C. 154(b) by 191 days.

(21) Appl. No.: 09/465,653

(22) Filed: Dec. 17, 1999

(51) Int. Cl.[7] .......................... A61K 35/78; A01N 25/00
(52) U.S. Cl. ...................... 424/725; 514/825; 514/817; 514/969; 514/946; 514/947; 514/783
(58) Field of Search ................................. 514/825, 817, 514/969, 946, 947, 783; 424/195.1, 725

(56) References Cited

U.S. PATENT DOCUMENTS

| | | | | | |
|---|---|---|---|---|---|
| 4,440,777 A | * | 4/1984 | Zupan | ........................ | 424/274 |
| 4,560,553 A | * | 12/1985 | Zupan | ........................ | 424/78 |
| 4,587,123 A | * | 5/1986 | Price | ........................ | 424/195.1 |
| 4,822,595 A | * | 4/1989 | Corliss et al. | ................ | 424/61 |
| 4,919,934 A | * | 4/1990 | Deckner et al. | ............ | 424/401 |
| 5,073,366 A | * | 12/1991 | Beck | ........................ | 424/720 |
| 5,223,257 A | * | 6/1993 | Arora | ...................... | 424/195.1 |
| 5,667,799 A | * | 9/1997 | Caldwell et al. | ........... | 424/449 |
| 5,889,049 A | * | 3/1999 | Juergens | ..................... | 514/510 |

FOREIGN PATENT DOCUMENTS

| | | | | |
|---|---|---|---|---|
| WO | WO-90/07331 | * | 7/1990 | ........... A61K/31/20 |

* cited by examiner

Primary Examiner—Theodore J. Criares
Assistant Examiner—Gina C. Yu
(74) Attorney, Agent, or Firm—John D. Gugliotta

(57) ABSTRACT

A composition for topical analgesic and antiseptic use which consists essentially of a approximately equal proportions of alcohol, turpentine, and eucalyptus oil.

7 Claims, No Drawings

TOPICAL COMPOSITION FOR ANTISEPTIC AND ANALGESIC PURPOSES

RELATED APPLICATIONS

The present invention was first described in Disclosure Document Number 455,333 filed on Apr. 23, 1999. There are no previously filed, nor currently any co-pending applications, anywhere in the world.

BACKGROUND OF THE INVENTION

1. Field of the Invention

The present invention relates generally to topical analgesic compositions and, more particularly, to a topical analgesic composed of eucalyptus oil, alcohol, and turpentine.

2. Description of the Related Art

In the related art, many other liquid analgesic and antiseptic compounds are known and disclosed. For example, U.S. Pat. No. 4,560,553 issued in the name of Zupan and U.S. Pat. No. 4,440,777 issued in the name of Zupan both disclose the use of eucalyptol for enhancing skin permeation of bio-affecting agents.

U.S. Pat. No. 5,667,799 issued in the name of Caldwell et al. describes a method of relieving headaches with topical application of an anesthetic comprised in part of eucalyptol.

U.S. Pat. No. 5,223,257 issued in the name of Arora discloses a topical composition for relieving aches and pains comprised in part of eucalyptus and alcohol.

U.S. Pat. No. 5,073,366 issued in the name of Beck describes an analgesic composition for providing temporary relief from arthritis comprised in part of eucalyptus and a low carbon alcohol.

U.S. Pat. No. 4,822,595 issued in the name of Corliss et al. discloses a hoof lotion for killing or preventing fungal growth comprised in part of turpentine.

U.S. Pat. No. 4,587,123 issued in the name of Price describes a composition for reducing pest infestation for topical application to animals comprised of eucalyptus, alcohol, and water.

However, in spite of these related disclosures, no topical composition for antiseptic and analgesic purposes is known that has been drawn around a topical analgesic composed of eucalyptus oil, alcohol, and turpentine.

SUMMARY OF THE INVENTION

It is therefore an object of the present invention to provide an improved topical analgesic and antiseptic liquid.

It is a feature of the present invention to provide a mixture of alcohol, turpentine, and eucalyptus oil. When mixing and processing of the components is complete, it would be used by rubbing the compound into the skin of the general area or by using it as a soak in a bath. It will aid in the reduction of pain from sore muscles, bruised tendons, lower back pain, arthritis and other similar ailments. The use of the present invention relieves the pain and associated suffering from common everyday aches, and allows one to continue life in a normal manner.

DETAILS OF THE PREFERRED EMBODIMENTS

A topical composition for antiseptic and analgesic purposes made according to the preferred embodiment of the present invention is comprised of three main ingredients: alcohol, turpentine, and eucalyptus oil. Although the preferred embodiment constitutes approximately equal proportions of each ingredient, it is envisioned that the features and benefits desired by the present invention can be accomplished when utilizing an amount of alcohol from about 25 percent to 40 percent, turpentine in an amount from about 40 percent to 25 percent, and eucalyptus oil in an amount of 50 percent to 20 percent respectively.

Although the noted components may be the sole components fo the composition, they are optionally combined with any suitable carrier so that the resulting composition is in the form of a lotion, cream, ointment, or salve.

When mixing and processing of the components is complete, it would be used by rubbing the compound into the skin of the general area or by using it as a soak in a bath. It will aid in the reduction of pain from sore muscles, bruised tendons, lower back pain, arthritis and other similar ailments. The use of the present invention relieves the pain and associated suffering from common everyday aches, and allows one to continue life in a normal manner.

The foregoing description is included to illustrate the operation of the preferred embodiment and is not meant to limit the scope of the invention. The scope of the invention is to be limited only by the following claims.

What is claimed is:

1. A composition which consists essentially of a combination of:
   a. Alchohol;
   b. Turpentine; and
   c. Eucalyptus Oil;
and wherein said combination comprises approximately equal proportions by volume of each element.

2. The composition of claim 1, wherein said alcohol is isopropyl alcohol.

3. A composition which consists essentially of a combination of:
   a. Alchohol;
   b. Turpentine; and
   c. Eucalyptus Oil;
and wherein said combination comprises an amount of alcohol from about 25 percent to 40 percent by volume.

4. A composition of claim 3, wherein said combination comprises turpentine in an amount of about 40 percent to 25 percent by volume.

5. A composition of claim 3, wherein said combination comprises eucalyptus oil in an amount of 50 percent to 20 percent by volume.

6. A topically administrable composition of claim 1 in the form of a lotion, cream, ointment, or salve.

7. A topically administrable composition of claim 3 in the form of a lotion, cream, ointment, or salve.

* * * * *